(12) United States Patent
Bertoni

(10) Patent No.: US 10,625,003 B2
(45) Date of Patent: Apr. 21, 2020

(54) METHOD FOR FILLING CONTAINERS WITH FRESH BLOOD COMPONENTS

(71) Applicant: Biomed Device S.R.L., Modena (MO) (IT)

(72) Inventor: Marco Bertoni, Modena (IT)

(73) Assignee: Biomed Device S.R.L., Modena (IT)

(*) Notice: Subject to any disclaimer, the term of this patent is extended or adjusted under 35 U.S.C. 154(b) by 517 days.

(21) Appl. No.: 15/536,174

(22) PCT Filed: Dec. 16, 2015

(86) PCT No.: PCT/IB2015/059665
§ 371 (c)(1),
(2) Date: Jun. 15, 2017

(87) PCT Pub. No.: WO2016/098007
PCT Pub. Date: Jun. 23, 2016

(65) Prior Publication Data
US 2017/0368243 A1 Dec. 28, 2017

(30) Foreign Application Priority Data
Dec. 16, 2014 (IT) .............................. MO2014A0360

(51) Int. Cl.
*A61M 1/02* (2006.01)
*A61J 1/20* (2006.01)

(52) U.S. Cl.
CPC .......... *A61M 1/0209* (2013.01); *A61J 1/2058* (2015.05); *A61M 1/0272* (2013.01)

(58) Field of Classification Search
CPC ............................ A61J 1/2058; A61M 1/0272
See application file for complete search history.

(56) References Cited

U.S. PATENT DOCUMENTS

2003/0052065 A1  3/2003  Rosiello

FOREIGN PATENT DOCUMENTS

| WO | WO2011/095964 | 8/2011 |
| WO | WO2012/123810 | 9/2012 |
| WO | WO2014/108852 | 7/2014 |

OTHER PUBLICATIONS

International Search Report dated Apr. 22, 2016 from the International Searching Authority Re. Application No. PCT/IB2015/059665. (3 pages).

*Primary Examiner* — Leslie R Deak

(57) ABSTRACT

A method for filling containers with fresh blood components, comprising the following steps of:
a) providing a piece of equipment (1) defining a transit channel (3) having at least a first gap (3a) associated with a bag (5) or the like containing a fresh blood component, at least a second gap (3b) connected to a plurality of containers (6) to be filled, and at least a third gap (3c) connected to pumping means (12);
b) isolating the first gap (3a) from the second gap (3b) and placing the latter in communication with the third gap (3c);
c) suctioning the air contained in the containers (6) to be filled by means of the pumping means (12) so as to define a vacuum inside them;
d) placing the first gap (3a) in communication with the second gap (3b), the containers (6) suctioning the contents of the bag (5) by effect of the vacuum defined inside them;
and where the channel (3) has at least a fourth gap (3d) associated with an empty syringe (4) or the like, and by the fact that it comprises, after step d), the following steps of:
e) isolating the first gap (3a) from the second gap (3b) and placing the first gap itself in communication with the fourth gap (3d);

(Continued)

f) taking at least a part of the contents of the bag (5) by means of the syringe (4);

g) isolating the fourth gap (3*d*) from the first gap (3*a*) and placing the fourth gap itself in communication with the second gap (3*b*);

h) sending the contents taken with the syringe (4) into the containers (6).

7 Claims, 2 Drawing Sheets

METHOD FOR FILLING CONTAINERS WITH FRESH BLOOD COMPONENTS

RELATED APPLICATIONS

This application is a National Phase of PCT Patent Application No. PCT/IB2015/059665, having International filing date of Dec. 16, 2015, which claims the benefit of priority of Italian Patent Application No. MO2014A000360, filed on Dec. 16, 2014. The contents of the above applications are all incorporated by reference as if fully set forth herein in their entirety.

FIELD AND BACKGROUND OF THE INVENTION

The present invention relates to a method for filling containers with fresh blood components such as, e.g., serum-eye drops, platelet-rich plasma, etc. . . .

To date, fresh blood components, in particular autologous blood components, are generally introduced into suitable containers, of the type of micro test tubes having relative closing caps, insulin syringes and vials, from which an operator then withdraws the desired quantity and introduces this individually inside a plurality of containers intended for use on the patient.

Since these operations involve transferring blood components from one container to another, and therefore their passage into the external environment, they must of course be performed in a sterile environment. Furthermore, the removal and storage of these containers does not guarantee their adequate storage and administration to the patient in a safe way, with loss of sterility and consequent risks of contamination of the product which considerably increases the risks of infection for the patient.

The preparation of such containers must be performed by trained medical or nursing staff inasmuch as the therapeutic efficacy of the product is strongly affected by the standards and procedures used to perform the above phases.

It follows, therefore, that this known method for the preparation of containers with fresh autologous blood components besides being complex to make is also unsafe from the health point of view and is therefore not feasible on the basis of the regulations in force. In fact, the correct performance of the operations described above is closely related to the ability of the personnel in charge and to the environment in which they are performed. These factors appear to be extremely limiting, inasmuch as they expose the preparation of the containers with autologous blood components to various risks.

Another known method for the preparation of containers with autologous blood components includes the filling of a duct (dialysis tubing) made of plastic material and the closure of this duct, e.g. by sealing, at a plurality of zones arranged in succession the one to the other and spaced apart the one from the other, so as to form a plurality of closed units.

These units are then opened, before their use, by cutting one of their respective ends, e.g. using scissors, in such a way as to make their content available for use.

This second method for the preparation of units containing platelet concentrate has a number of drawbacks.

More in particular, the units of known type are not easy and safe to use and do not permit compliance with the hygienic-health standards required by applicable laws as well as by blood product certification bodies.

In fact, the opening of these units by means of scissors or the like, entails that on the cutting zone of such scissors residues remain of the organic material contained in the relative unit, with the consequent risk of contaminating the contents of the other units subsequently cut using the same scissors.

This obviously creates the risk of the platelet contents of the units cut by means of previously-used scissors becoming polluted by the residues left on the scissors themselves, thus compromising their therapeutic properties and above all significantly increasing the risk of developing secondary infections in already immunosuppressed patients and in an already-compromised organ.

SUMMARY OF THE INVENTION

The main aim of the present invention is to provide a method for filling containers with fresh blood components which is practical and safe to use.

Within such aim, one object of the present invention is to provide a method for filling containers with fresh blood components which permits compliance with the hygienic-health standards required by applicable laws.

Another object of the present invention is to avoid any risk of external contamination of the blood components during the operation of transfer inside the containers to be filled (aliquotation in closed system).

Yet another object of the present invention is to free as much as possible the correct filling of the containers from the ability of the operator and from the environment in which such filling is performed.

Another object of the present invention is to provide a method for filling containers with fresh blood components which allows to overcome the mentioned drawbacks of the prior art within the ambit of a simple, rational, easy, effective to use as well as affordable solution.

The objects stated above are achieved by the present method for filling containers with fresh blood components according to claim 1.

BRIEF DESCRIPTION OF THE SEVERAL VIEWS OF THE DRAWINGS

Other characteristics and advantages of the present invention will become better evident from the description of a preferred, but not exclusive, embodiment of a piece of equipment for implementing the method according to the invention, illustrated by way of an indicative, but non-limiting example in the accompanying drawings, in which.

DESCRIPTION OF SPECIFIC EMBODIMENTS OF THE INVENTION

Figure 1:
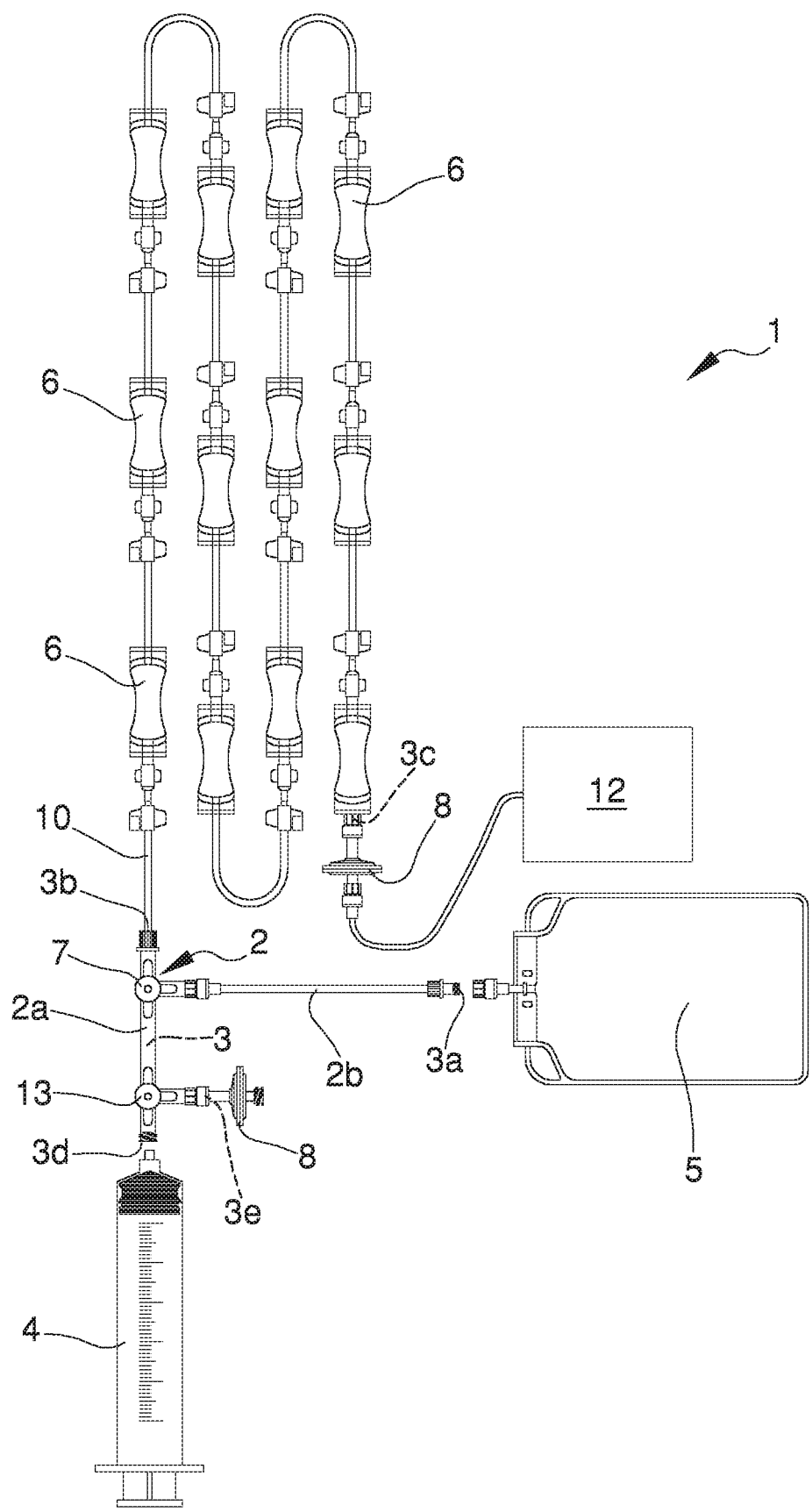
FIG. 1 is a top plan view of a piece of equipment for implementing the method according to the invention, in a first embodiment.

With particular reference to such figures, reference number 1 globally indicates a piece of equipment for filling containers with fresh blood components. The equipment making the subject of the present invention is particularly suitable in the case of fresh autologous blood components, although its use with fresh homologous blood components cannot be ruled out.

The equipment 1 comprises at least one tubular element 2 which defines a transit channel 3.

The channel 3 has at least a first gap 3a associated with a bag 5 or the like containing a fresh blood component, at least a second gap 3b connected to a plurality of containers 6 to be filled and at least a third gap 3c connected to pumping means 12. Conveniently, between the third gap 3c and the pumping means 12 is placed at least one antibacterial and hydrophobic filtering element 8, able to prevent impurities from entering inside the containers 6.

The bag 5 can also be replaced with a syringe.

More in detail, in the embodiments shown in the illustrations, the tubular element 2 has at least one main section 2a, from which extends at least a derivation 2b defining the first gap 3a.

Advantageously, the channel 3 also has a fourth gap 3d associated with an empty syringe 4 or the like.

Conveniently, the fourth gap 3d is defined along the main section 2a and is arranged opposite the second gap 3b with respect to the derivation 2b.

Preferably, the equipment 1 comprises first valve means 7 arranged along the channel 3 and operable to place in communication/isolate at least the first gap 3a with/from the second gap 3b.

More in detail, the first valve means 7 can be moved between a first configuration of use, wherein the first and the second gap 3a and 3b are placed in communication, and a second configuration of use, wherein the first and the second gap 3a and 3b are isolated.

In the embodiment shown in the illustrations, the first valve means 7 are operable to selectively place in communication the gaps 3a, 3b and 3d. In this preferred embodiment, the first valve means 7 can be moved between a first configuration of use, wherein the first gap 3a is placed in communication with the second gap 3b and the fourth gap 3d is isolated, a second configuration of use, wherein the first gap 3a is placed in communication with the fourth gap 3d and the second gap 3b is isolated, and a third configuration of use, wherein the second gap 3b is placed in communication with the fourth gap 3d and the first gap 3a is isolated. The first valve means 7 are, e.g., of the type of a three-way cock.

Advantageously, the equipment 1 can also comprise second valve means 9 arranged at the third gap 3c and operable to place in communication/isolate the third gap itself with/from the second gap 3b.

In the first embodiment shown in FIG. 1, the channel 3 has a single second gap 3b, with which is associated a supply duct 10 along which are arranged a plurality of containers 6 in series the one to the other. In this embodiment, the third gap 3c is defined at the last of the containers 6 placed farther away from the second gap 3b. The third gap 3c is constantly open, although alternative embodiments cannot be ruled out wherein the second valve means described above are provided.

In this first embodiment, the channel 3 has a further gap 3e communicating with the outside, placed between the first gap 3a and the fourth gap 3d and inside which is inserted a filtering element 8 able to prevent impurities from entering inside the channel 3. As can be seen from FIG. 1, the equipment 1 also comprises third valve means 13 arranged along the channel 3 and operable at least to place in communication/isolate the fourth gap 3d with/from the further gap 3e.

More particularly, the second valve means 9 can be moved between at least a first configuration of use, wherein the fourth gap 3d is in communication with the further gap 3e and is isolated from the other gaps 3a and 3b, and at least a second configuration of use, wherein the further gap 3e is isolated from the other gaps 3a, 3b and 3d. The second valve means 9 can also have further configurations of use able to isolate the further gap 3e from the fourth gap 3d and to place it in communication, depending on the configuration taken by the first valve means 7, with at least one of the first and the second gap 3a and 3b. The second valve means 9 are also, e.g., of the type of a three-way cock.

Figure 2:
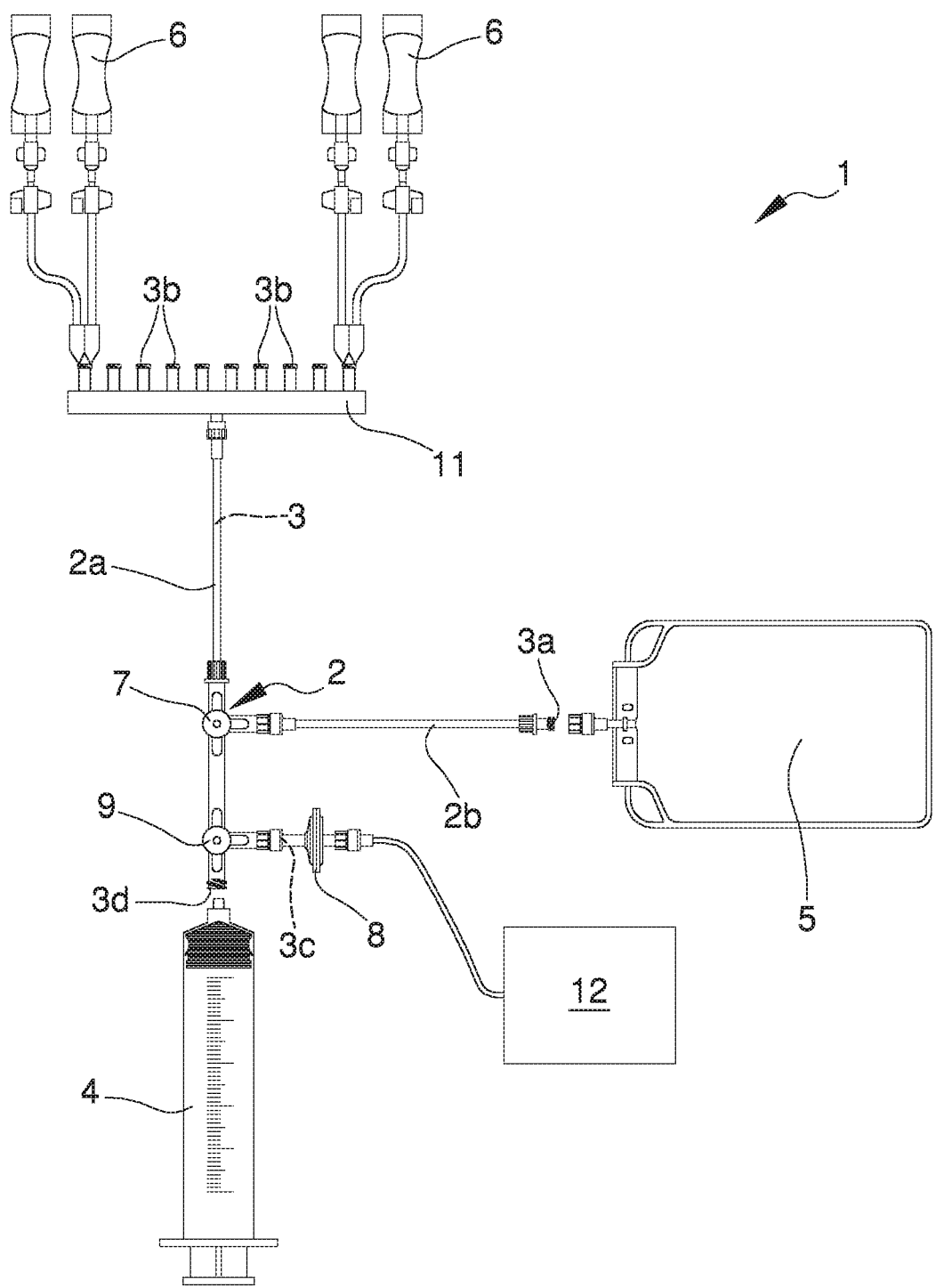
FIG. 2 is a top plan view of a piece of equipment for implementing the method according to the invention, in a second embodiment.

In the second embodiment shown in FIG. 2, the tubular element 2 comprises a connecting element 11 which defines a plurality of second gaps 3b to which the containers 6 to be filled are connected. As can be seen from FIG. 2, the second gaps 3b are arranged in parallel to one another.

In this second embodiment, the third gap 3c is arranged upstream of the second gaps 3b. More particularly, the third gap 3c is placed between the first gap 3a and the fourth gap 3d.

As can be seen from FIG. 2, at the third gap 3c there are also second valve means 9 which provide three configurations of use of which a first configuration able to place the third gap 3c in communication with the fourth gap 3d and is isolated from the other gaps 3a, 3b, a second configuration wherein the third gap 3c is isolated from the other gaps 3a, 3b, 3d, and a third configuration wherein, depending on the position taken by the first valve means 7, the third gap 3c can be placed in communication with the first gap 3a or with the second gaps 3b.

The operation of the equipment 1 in the execution of the method according to the invention is described below.

The method forming the subject of the present invention first of all provides that the first gap 3a be isolated from the second gap 3b (or from the second gaps 3b in the second embodiment of FIG. 2).

Subsequently, the air contained in the containers 6 is suctioned by means of the pumping means 12 so as to define a vacuum inside them.

In the first embodiment this step is performed by simply activating the pumping means 12. This way it is also possible to check the seal of the line, i.e., verify the absence of leaks along the supply duct 10 or in the containers 6.

In the case of the occurrence of a breakage or malfunction of the pumping means 12 and of the equipment 1 being also provided with the syringe 4 as described above, the air contained in the containers 6 can be suctioned by operating the third valve means 13 so as to place in communication the fourth gap 3d with the second gap 3b so as to allow the suctioning of the air contained in the containers 6 and, subsequently, the fourth gap 3d with the further gap 3e so as to allow the expulsion of the suctioned air by means of the syringe 4.

In the second embodiment, on the other hand, to suction the air contained in the containers 6 the first and second valve means 7 and 9 have to be brought to the respective third configurations of use, then activating the pumping means 12. Also in this case, if a malfunction of the pumping means 12 occurs, the air contained in the containers 6 can be suctioned through the syringe 4.

Once the air contained in the containers 6 has been suctioned, the first gap 3a is placed in communication with the second gap 3b in such a way that the vacuum defined inside of the containers themselves causes a recall action on the blood component contained in the bag 5 which is suctioned by the containers themselves. This step is performed by bringing the first valve means 7 to their first configuration of use.

More in detail, in the first embodiment, the substance contained in the bag 5 is introduced inside the channel 3 and enters inside the containers 6 passing through the second gap 3b. Containers 6 are then filled in succession as a result of the introduction of the blood component contained in the bag 5 in the channel 3.

In the second embodiment shown in FIG. 2, on the other hand, the substance contained in the bag 5 is introduced inside the channel 3 and enters substantially simultaneously inside the containers 6 passing through the respective second gaps 3b.

It may become necessary to introduce a further quantity of the blood component contained in the bag 5 inside the containers 6.

In this case, in the first embodiment of FIG. 1 this further addition can be introduced through the pumping means 12 or, alternatively, by means of the syringe 4.

In the second embodiment, on the other hand, the further addition of the blood component is performed by acting on the syringe 4, having previously operated the first and second valve means 7 and 9.

The steps of filling the syringe 4 with the contents of the bag 5 and the subsequent conveying of such content inside the containers 6 can be repeated until the complete filling of the containers themselves.

It has in practice been ascertained how the described invention achieves the proposed objects and in particular the fact is underlined that the method and the equipment forming the subject of the present invention allow filling in an easy and safe way a plurality of containers with fresh blood components.

In particular, the equipment according to the invention permits suctioning the air contained in the containers to be filled in an easy, practical and quick way.

Furthermore, the equipment in question allows defining a closed and sterile path inside which the fresh autologous blood component is made to circulate which, for that reason, permits avoiding any type of external contamination.

Again, the steps of the method forming the subject of the present invention permit filling in an extremely quick and safe way a plurality of containers and, moreover, ensure that such operations are successful irrespective of the skill of the operator who performs them and of the environment in which the relative equipment is located.

The invention claimed is:

1. A method for filling containers with fresh blood components, wherein it comprises the following steps of:
a) providing a piece of equipment (1) defining a transit channel (3) having at least a first gap (3a) associated with a bag (5) or the like containing a fresh blood component, at least a second gap (3b) connected to a plurality of containers (6) to be filled, and at least a third gap (3c) connected to pumping means (12);
b) isolating said first gap (3a) from said second gap (3b) and placing the latter in communication with said third gap (3c);
c) suctioning the air contained in said containers (6) to be filled by means of said pumping means (12) so as to define a vacuum inside them;
d) placing said first gap (3a) in communication with said second gap (3b), said containers (6) suctioning the contents of said bag (5) by effect of the vacuum defined inside them;
and wherein said channel (3) has at least a fourth gap (3d) associated with an empty syringe (4) or the like, and by the fact that it comprises, after step d), the following steps of:
e) isolating said first gap (3a) from said second gap (3b) and placing the first gap itself in communication with said fourth gap (3d);
f) taking at least a part of the contents of said bag (5) by means of said syringe (4);
g) isolating said fourth gap (3d) from said first gap (3a) and placing the fourth gap itself in communication with said second gap (3b);
h) sending the contents taken with said syringe (4) into said containers (6).

2. A method according to claim 1, wherein said containers (6) are arranged in series the one to the other, wherein said third gap (3c) is defined at the extremity of the last of said containers (6) placed farther away from said second gap (3b) and by the fact that it comprises, after step d), the following step of:
i) suctioning further contents from said bag (5) by means of said pumping means (12).

3. A method according to claim 1, wherein it comprises a plurality of said second gaps (3b), said containers (6) being arranged in parallel to one another, and by the fact that said third gap (3c) is arranged upstream of said second gaps (3b).

4. A method according to claim 1, wherein said equipment (1) comprises at least first valve means (7) operable to place said first gap (3a) in communication/isolate with/from said second gap (3b), at least said steps b) and d) being performed by operating said first valve means (7).

5. A method according to claim 1, wherein said third gap (3c) is constantly in communication with said second gap (3b).

6. A method according to claim 4, wherein said equipment (1) comprises second valve means (9) arranged at said third gap (3c) and operable to place the third gap itself in communication/isolate with/from said second gap (3b), at least said step b) being performed by operating said second valve means (9).

7. A method according to claim 6, wherein said second valve means (9) are operable to selectively place said third gap (3c) and said fourth gap (3d) in communication with said second gap (3b).

* * * * *